(12) United States Patent
Tsutsui et al.

(10) Patent No.: US 6,973,352 B1
(45) Date of Patent: Dec. 6, 2005

(54) STEERABLE CARDIAC PACING AND SENSING CATHETER AND GUIDEWIRE FOR IMPLANTING LEADS

(75) Inventors: Duane Tsutsui, West Hills, CA (US); Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 530 days.

(21) Appl. No.: 10/313,699

(22) Filed: Dec. 5, 2002

(51) Int. Cl.7 .................................................. A61N 1/00
(52) U.S. Cl. ...................................................... 607/122
(58) Field of Search ................................. 607/115–132

(56) References Cited

U.S. PATENT DOCUMENTS

| | | | |
|---|---|---|---|
| 5,462,544 A | 10/1995 | Saksena et al. | 606/15 |
| 5,549,109 A | 8/1996 | Samson et al. | 128/642 |
| 5,722,425 A | 3/1998 | Boström | 128/772 |
| 5,728,148 A | 3/1998 | Boström et al. | 607/116 |
| 5,752,915 A | 5/1998 | Neubauer et al. | 600/373 |
| 5,755,766 A | 5/1998 | Chastain et al. | 607/122 |
| 5,807,339 A | 9/1998 | Boström et al. | 604/164 |
| 6,203,506 B1 | 3/2001 | Boström | 600/585 |
| 6,456,889 B2 | 9/2002 | Pianca et al. | 607/122 |
| 6,456,890 B2 | 9/2002 | Pianca et al. | 607/122 |
| 2001/0037136 A1 | 11/2001 | Pianca et al. | 607/122 |

*Primary Examiner*—Scott M. Getzow

(57) ABSTRACT

An assist device for an implantable cardiac stimulation lead system includes a handle for a steerable guidewire system. An inner conductive guidewire with a distal tip electrode is pre-shaped into a free state curved configuration. An outer sheath is coaxial with the guidewire and relatively slidable between a first position restraining the guidewire to a straight condition and a second position withdrawn from a freed length of the guidewire allowing it to assume its free state curved condition. A collar on the outer sheath is movable along the handle for moving the sheath between the first and second positions. An electrical terminal is in electrical continuity with the tip electrode such that a pacing system analyzer connected between the electrical terminal and a reference electrode in the body is operable for seeking a location at which optimal pacing parameters can be determined prior to final implantation of the lead system.

16 Claims, 5 Drawing Sheets

STEERABLE CARDIAC PACING AND SENSING CATHETER AND GUIDEWIRE FOR IMPLANTING LEADS

FIELD OF THE INVENTION

The present invention relates generally to an implantable lead for use with an implantable medical device and, more particularly, to a technique for seeking a location at which optimal pacing parameters can be determined prior to final implantation of the lead.

BACKGROUND OF THE INVENTION

Permanently implantable electrical lead systems are used in conjunction with implantable medical devices, such as pacemakers and defibrillators. In these applications the lead is used to transmit electrical signals to and/or from the medical device. Leads of this type may be chronically implanted and are expected to exhibit a long service life in a hostile environment of the human body. Cardiac stimulation leads are usually implanted via the cardiovascular venous system such that the distal end of the lead is positioned at an appropriate site within a heart chamber or within cardiac coronary vasculature which overlie the epicardial surface of the heart.

Cardiac leads currently are typically either unipolar pacing and/or sensing leads constructed with a single coil electrical conductor and an outer extruded insulation tube; or they are bipolar coaxially constructed with an inner coil electrical conductor, an inner insulation tube around the inner coil; and an outer coil electrical conductor surrounded by its outer extruded insulation tube. Cardiac leads may also be a combination pacing and/or sensing and/or defibrillation lead which may utilize one lumen to house a guidewire used for lead implantation maneuvering and lead tip placement and one or more additional lumina to house one or more coil and/or cable electrical conductors. In another instance, a conductor or conductors and a guidewire may share the same lumen.

The traditional lead includes a lead body having a generally circular exterior cross-section and one or more circular lumens, which may be arranged coaxially or parallel to one another. Typically, spiral wound metallic coil conductors are positioned within one or more lumens of the lead body. The spiral wound coil conductor also forms a lumen which can receive a stylet to help stiffen the lead as an aid to lead placement during lead implantation.

With currently available tools and techniques for placing leads through the coronary sinus and beyond, the physician is still presented with the challenge of which tributary or vascular pathway he or she should take that would yield optimal performance of the left heart lead. Many times, a physician would spend a significant amount of time to place the lead only to find that either capture thresholds are unacceptable or diaphragmatic stimulation is present. At this point, the physician has no choice but to reposition the lead in another vascular tributary which, if this process is repeated until a suitable tributary is found, will significantly increase the duration of the procedure. This invention disclosure will describe a tool that is designed to significantly reduce the time it takes to identify an optimal location for the left heart lead by allowing the physician to take electrical measurements, thereby identifying exactly which tributary to follow before the lead is even inserted into the patient.

In order to fully appreciate the advance provided by the present invention, it is desirable to review the state of the prior art prior to its conception. Thus, known constructions of heart tissue mapping catheters well suited for control of tachyarrhythmias are disclosed in U.S. Pat. No. 5,462,544 to Saksena et al. and to U.S. Pat. No. 5,549,109 to Samson et al. Various devices for manipulating a stylet unit having a stylet movable within a stylet sleeve for selectively positioning an electrode cable in a body cavity are disclosed, variously, in U.S. Pat. No. 5,722,425 to Boström, U.S. Pat. No. 5,728,148 to Boström et al., U.S. Pat. No. 5,752,915 to Neubauer et al., U.S. Pat. No. 5,807,339 to Boström et al., and U.S. Pat. No. 6,203,506 to Boström. U.S. Publication No. 2001/0037136 to Pianca et al. discloses an implantable lead for electrical stimulation of the body which includes an elongated multi-lumen tube with a distal tip electrode having a longitudinally extending central bore. A cable conductor is received in one lumen of the multi-lumen tube for electrical connection to the tip electrode and an elongated polymeric tubular liner is received in another lumen of the multi-lumen tube generally aligned with the bore of the distal tip electrode for freely receiving a guidewire through the tubular liner and through the bore of the distal tip electrode. An electrically conductive proximal pin is attached to the multi-lumen tubing distant from the tip electrode and the cable conductor and the proximal end of the polymeric tubular liner are attached to the proximal pin. Initially, the guidewire is implanted into the body along a desired trajectory. With the polymeric tubular liner inserted, first the distal tip electrode, then the remainder of the multi-lumen tube, are slid onto the guidewire such that the guidewire slidably advances within the polymeric tubular liner. Thereupon, the multi-lumen tube is advanced along the guidewire until a desired site is achieved and the guidewire is removed from the body and the multi-lumen tube.

It was in light of the foregoing that the present invention was conceived and has now been reduced to practice.

SUMMARY OF THE INVENTION

An assist device for an implantable cardiac stimulation lead system includes a handle for a steerable guidewire system. An inner conductive guidewire with a distal tip electrode is pre-shaped into a free state curved configuration. An outer sheath is coaxial with the guidewire and relatively slidable between a first position restraining the guidewire to a straight condition and a second position withdrawn from a freed length of the guidewire allowing it to assume its free state curved condition. A collar on the outer sheath is movable along the handle for moving the sheath between the first and second positions. An electrical terminal is in electrical continuity with the tip electrode such that a pacing system analyzer connected between the electrical terminal and a reference electrode in the body is operable for seeking a location at which optimal pacing parameters can be determined prior to final implantation of the lead system.

The tool embodying the invention is a steerable cardiac pacing and sensing catheter that is of small enough diameter to also serve as a guidewire for guiding an over-the-wire lead to the previously tested location identified as a suitable location for placement of a left heart pacing lead. The design of this tool is based on a design which features a coaxial wire within a wire whereby the inner wire is pre-curved and takes the shape of the curve as the outer wire or sheath is pulled back exposing the inner wire and allowing it to curve. This feature allows steerability of the lead at the distal end.

In order to accomplish the task of taking measurements, the inner wire must be electrically insulated from the outer sheath and, likewise, the outer sheath must also be electrically insulated. In addition, the slide mechanism that withdraws the outer sheath must contain electrodes that can be connected to a pacing system analyzer (PSA) for measurements. Finally, the handle or steering mechanism must be detachable so as to leave only the wire that also serves as the guidewire for guiding an over-the-wire lead to the identified location within the vasculature, for example, on the left side of the heart.

The steerable catheter is advanced through the catheter delivery system into the coronary sinus and down one of the lateral veins using the steering mechanism. Once the steerable catheter is in position, a pacing system analyzer (PSA) is attached to the anode and cathode electrodes found on the handle and measurements are taken. If a location in the body is found not to be an ideal location, the steerable catheter can be retracted and again advanced into an alternate tributary until an acceptable location can be found. Once a location has been determined, the handle, or proximal end, of the steerable catheter can be rotated which will causes the handle to detach from the wire leaving only the wire itself. The wire can now be used as a guidewire. The distal end of the over-the-wire (OTW) lead can now be placed over the guidewire and fed through the inner lumen of the lead until the lead is in place. Measurements using the lead can now be taken and the guidewire can be removed.

A primary feature of the invention, then, is the provision of an assist system for a lead used with an implantable medical device which employs a technique for seeking a location at which optimal pacing parameters can be determined prior to final implantation of the lead.

Another feature of the present invention is the provision of such an assist system according to which a steerable catheter is advanced through the catheter delivery system into the coronary sinus and down one of the lateral veins using the steering mechanism, and once the steerable catheter is in position, a pacing system analyzer (PSA) is attached to the anode and cathode electrodes found on the handle and measurements are taken, then if a location in the body is found not to be an ideal location, the steerable catheter can be retracted and again advanced into an alternate tributary until an acceptable location can be found.

Still another feature of the present invention is the provision of such an assist system according to which, once a location has been determined, the handle, or proximal end, of the steerable catheter can be rotated which will causes the handle to detach from the wire leaving only the wire itself, the wire now being used as a guidewire with the distal end of the over-the-wire (OTW) lead now being placed over the guidewire and fed through the inner lumen of the lead until the lead is in place enabling measurements using the lead to taken, then the guidewire removed.

Yet another feature of the present invention is the provision of such an assist system which includes a handle for a steerable guidewire system, an inner conductive guidewire with a distal tip electrode pre-shaped into a free state curved configuration, an outer sheath coaxial with the guidewire and relatively slidable between a first position restraining the guidewire to a straight condition and a second position withdrawn from a freed length of the guidewire allowing it to assume its free state curved condition, a collar on the outer sheath movable along the handle for moving the sheath between the first and second positions, and an electrical terminal in electrical continuity with the tip electrode such that a pacing system analyzer connected between the electrical terminal and a reference electrode in the body is operable for seeking a location at which optimal pacing parameters can be determined prior to final implantation of the lead system.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
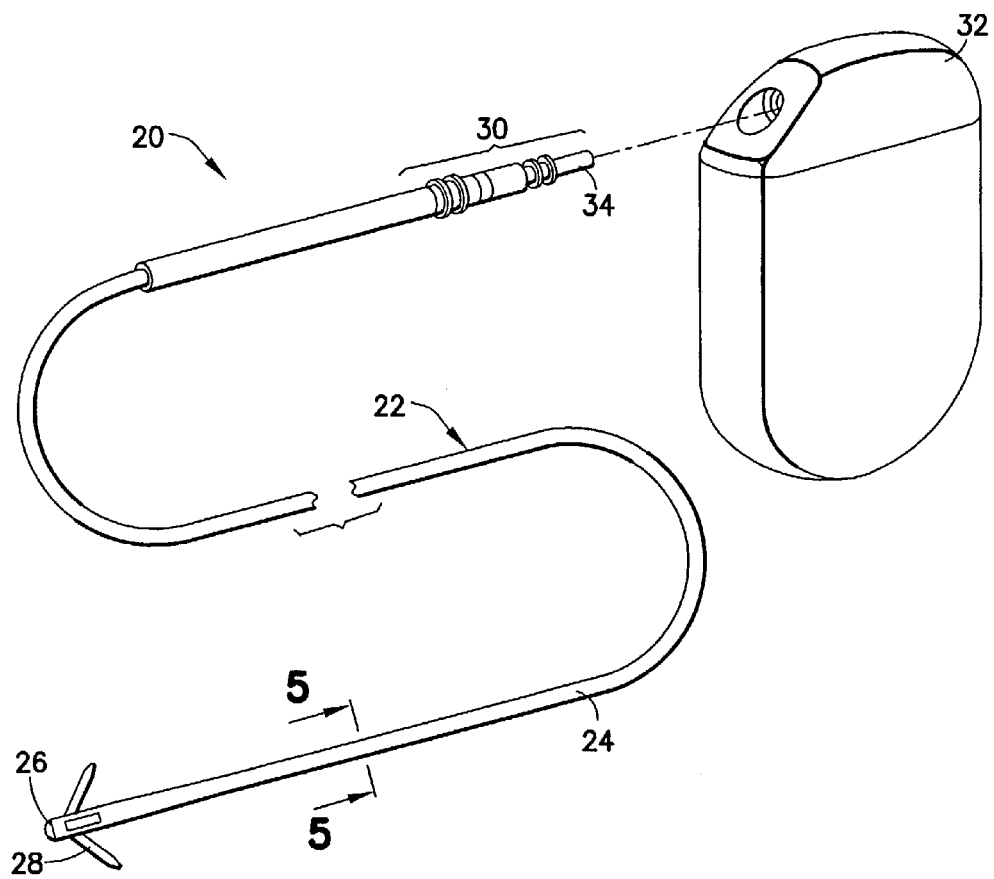
FIG. 1 is a is a perspective exploded view of a body implantable lead system embodying the invention positioned for engagement at one end with heart tissue and at the other end for insertion into a body stimulation device such as a pacemaker and/or defibrillator.

Turn now to the drawings and, initially to FIG. 1 which generally illustrates a body implantable lead system 20 of the endocardial type incorporating features of the present invention. Although the present invention will be described with reference to the embodiments shown in the drawings, it should be understood that the present invention can be embodied in many alternate forms or embodiments. In addition, any suitable size, shape or type of elements or materials consistent with the invention could be used.

The lead system 20, illustrated to be of a unipolar design, but not intended to be limiting of the invention, includes a lead body 22 with an insulating sheath 24 interconnecting a distal electrode 26 secured adjacent an interior wall of an organ such as the heart by means, for example, of fixing tines 28 which engage the tissue or trabeculae of the heart. The lead system 20 also includes an electrical connector 30 at a proximal end to which can be attached a source of electrical energy such as a pacemaker 32. In a known manner, connector pin terminal 34 is electrically in common with the cathode tip electrode 26 at the distal end of the lead. The insulating sheath 24 of the lead body 22 is composed of flexible biocompatible flexible polymeric insulating material such as silicone rubber, polyurethane, PTFE (polytetrafluoroethylene), or ETFE (ethyltetra fluoroethylene).

Figure 2:
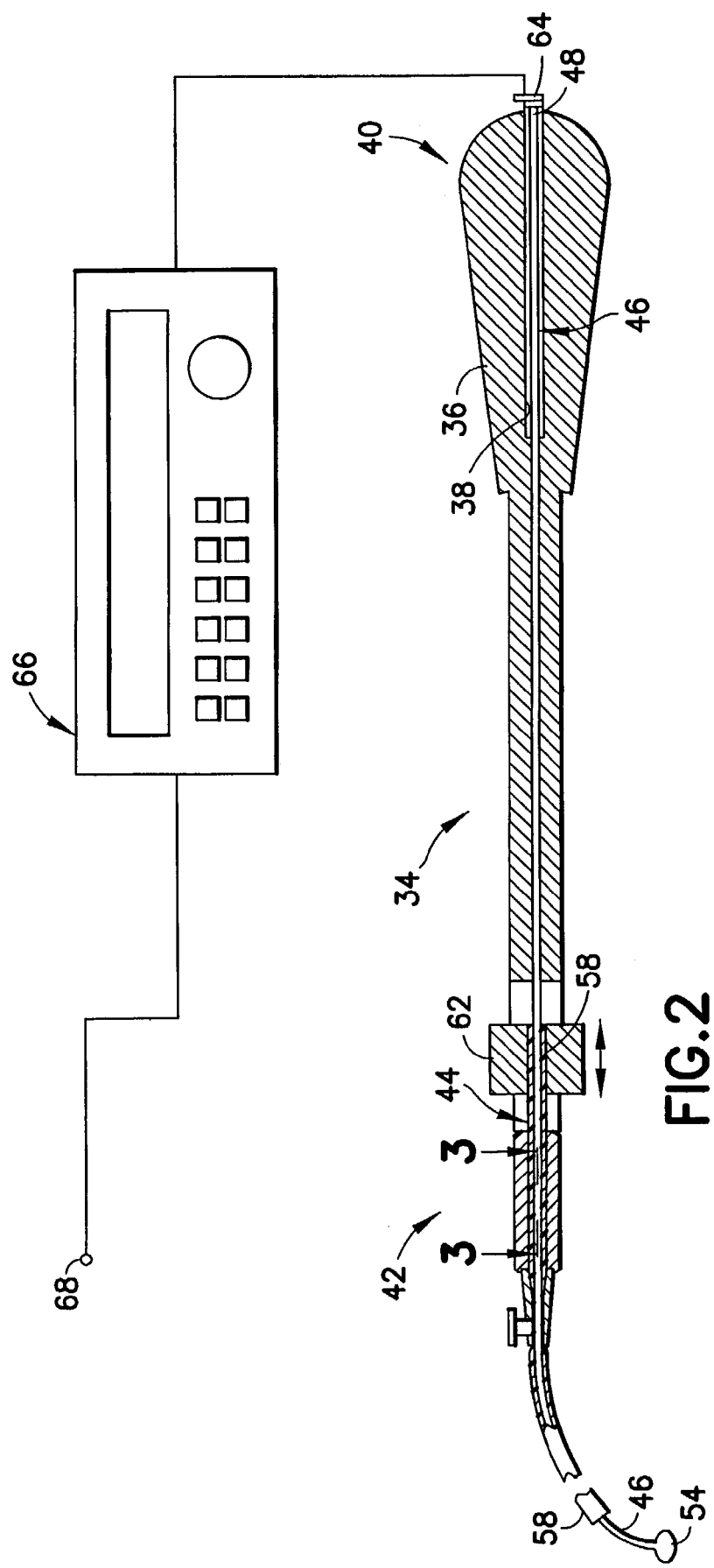
FIG. 2 is a diagrammatic and schematic view, partially cut away and in section, of an assist system according to the invention.

Turn now to FIG. 2 for the description of an assist device 34 for an implantable lead system such as the lead system 20 used for stimulating the body by way of the pacemaker 32. The assist device 34 is generally of known construction and includes an elongated handle 36 having a passage 38 extending longitudinally between a proximal end 40 and a distal end 42. The assist device also includes a steerable guidewire system 44 (FIGS. 2 and 3) slidably received in the longitudinally extending passage 38 of the elongated handle 36. An inner conductive guidewire 46 extends between a proximal end 48 (FIG. 2) and a distal end 50 (FIG. 4) having a peripheral outer surface 52 and pre-shaped into a curved configuration when in the free state (FIG. 4) but in FIG. 4A shown forced into a straight shape. The guidewire 46 includes a tip electrode 54 at its distal end.

Figure 3:
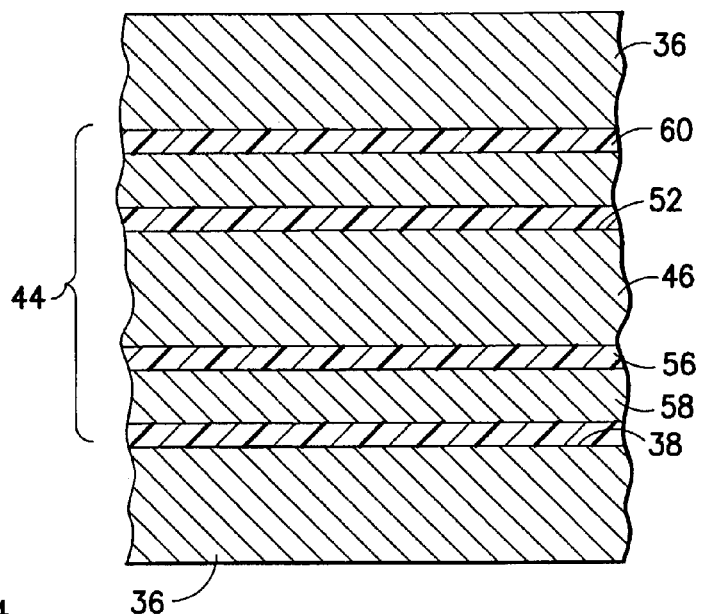
FIG. 3 is a cross section view taken generally along line 3—3 in FIG. 2.
Figure 4:
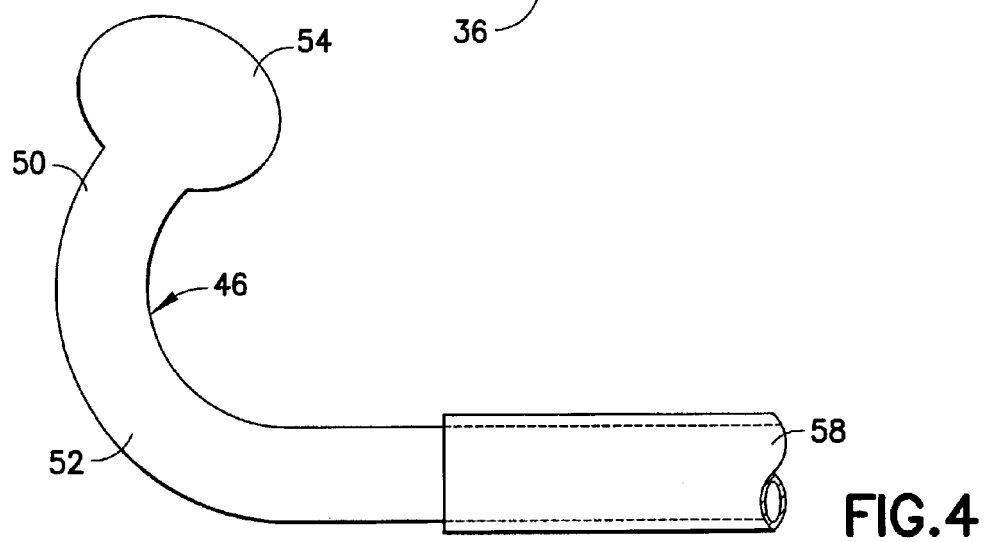
FIG. 4 is a detail side elevation view illustrating one position of relatively movable components of the invention.
Figure 4A:
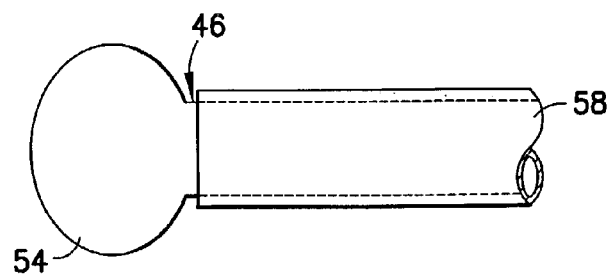
FIG. 4A is a detail side elevation view, similar to FIG. 4, illustrating another position of the relatively movable components of the invention.

Viewing FIG. 3, suitable inner insulation 56 covers the peripheral outer surface 52 of the conductive guidewire 46 and a longitudinally extending generally straight outer sheath 58 is coaxial with the conductive guidewire and is longitudinally slidable relative to the guidewire between a first position (FIG. 4A) completely receiving the conductive guidewire and thereby restraining the conductive guidewire to a straight condition and a second position (FIG. 4) withdrawn from a freed length of the conductive guidewire allowing the freed length to assume its free state curved condition. If the outer sheath 58 and the handle 36 are both metallic, it may be desirable for a suitable outer insulative covering 60 to be provided on the outer sheath.

Turning back to FIG. 2, the elongated handle 36 includes a collar 62 movable longitudinally along the handle and attached to the outer sheath 58 for manually moving the outer sheath between the first (FIG. 4A) and second (FIG. 4) positions with longitudinal movement along the handle. As modified in accordance with the invention, the assist device 34 includes an electrical terminal at the proximal end 48 of the handle 36 in electrical continuity with the tip electrode 54. With this construction, a pacing system analyzer (PSA) 66, a suitable instrument being PSA Model 3100, sold by SeaMed of Bellvue, Wash. connected between the electrical terminal 64 and a reference electrode 68 suitably positioned by the physician, for example, in the body is operable for seeking a location at which optimal pacing parameters can be determined prior to final implantation of the lead system 20. It will be understood by those skilled in the art that reference electrode 68 may also be placed on the surface of the body, or in any suitable location within the body.

Figure 5:
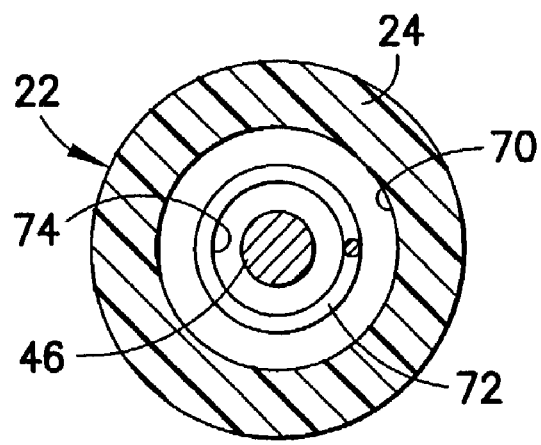
FIG. 5 is a cross section view taken generally along line 2—2 in FIG. 1.

The lead system 20 may take a variety of constructions. For example, viewing FIGS. 1 and 5, the elongated tubular lead body 22 is seen to include an insulating sheath 24 of flexible resilient insulative material extending between its proximal and distal ends and having a longitudinally extending lumen 70. The flexible polymeric insulating material of the insulating sheath 24 can be, variously, silicone rubber, polyurethane, PTFE, and ETFE, or combinations thereof, or of any other suitable material. As earlier noted, a distal tip electrode 26 is attached to the distal end of the lead body 22 and a coil conductor 72 is received in the lumen 70 of the lead body also extends between the proximal and distal ends of the lead body. The coil conductor is joined at its proximal end to the electrical connector 30 for selective connection to a cardiac stimulation device, or pacemaker, 32. In turn, the coil conductor 72 defines a second longitudinally extending lumen 74 for receiving the guidewire 46 for implantation of the lead system 20 after the optimal pacing parameters determined by the PSA 66 associated with the assist device 34 have been determined.

Figure 6:
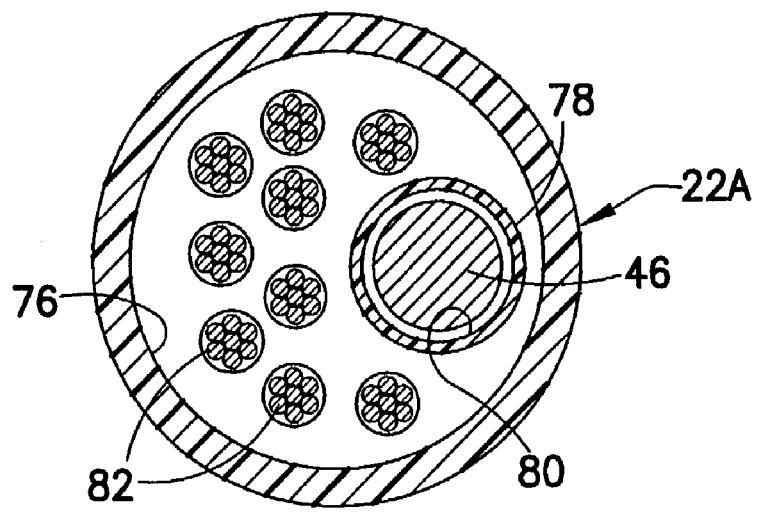
FIG. 6 is a cross section view, similar to FIG. 2 but illustrating another embodiment of the invention.

In another instance, turning now to FIG. 6, a modified lead system according to the invention includes an elongated tubular lead body 22A of flexible resilient insulative material extending between proximal and distal ends and having a first longitudinally extending lumen 76. As before, a distal tip electrode is attached to the distal end of the lead body although it is not illustrated in this instance. An elongated tubular member 78 of flexible resilient insulative material is received in the first lumen 76 of the tubular lead body and defines a second longitudinally extending lumen 80 for receiving the guidewire 46 therethrough for implantation of the lead system, again, as earlier explained, after optimal pacing parameters have been determined by the PSA 66 associated with the assist device 34. Also, as noted before, the flexible resilient insulative material in all instances may be variously, silicone rubber, polyurethane, PTFE, and ETFE, or combinations thereof, or of any other suitable material. In any event, in this instance, a plurality of insulated cable conductors 82 are received in the lumen 76 of the tubular lead body 22A and extend between the proximal and distal ends of the lead body.

Figure 7:
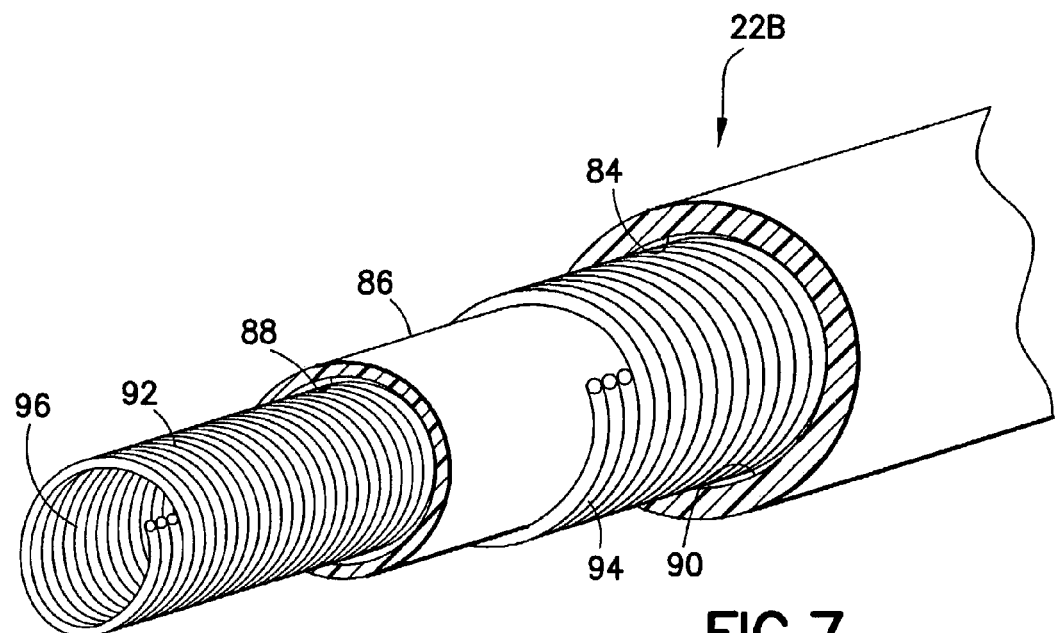
FIG. 7 is a perspective view, certain portions being cut away and shown in section, of another embodiment of the invention.

In still another instance, turning now to FIG. 7, a modified lead system according to the invention includes an elongated tubular lead body 22B of the afore-mentioned flexible resilient insulative material extending between proximal and distal ends and having a first longitudinally extending lumen 84. The lead body 22B also includes an elongated tubular member 86 of similarly constituted flexible resilient insulative material having a second longitudinally extending lumen 88 coaxial with the first lumen 84. The tubular member 86 has an outer diameter smaller than the inner diameter of the lead body 22B thereby defining an annular cavity 90. An inner coil conductor 92 is received within the second longitudinally extending lumen and extends between the proximal and distal ends of the lead body and an outer coil conductor 94 received within the annular cavity 90 also extends between the proximal and distal ends of the lead body. The inner coil conductor 92 defines a third longitudinally extending lumen 96 for receiving therethrough a guidewire 46 (though not shown in this view) for implantation of the lead system after optimal pacing parameters have been determined in the manner earlier explained.

Figure 8:
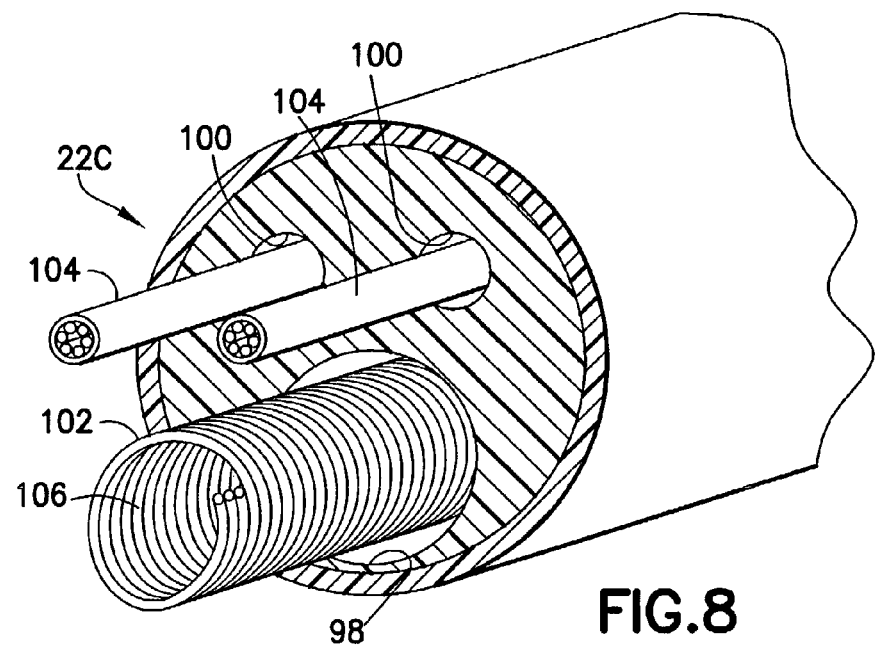
FIG. 8 is a perspective view, certain portions being cut away and shown in section, of still another construction of the invention.

In yet another instance, turning now to FIG. 8, a modified lead system according to the invention includes a modified elongated tubular lead body 22C, again, of flexible resilient insulative material having first and second longitudinally extending lumina, 98, 100, respectively. In this instance, a coil conductor 102 is received within the first longitudinally extending lumen 98 and extends between the proximal and distal ends of the lead body. A cable conductor 104 is received in each second lumen 100 and each cable conductor extends between the proximal and distal ends of the lead body. The coil conductor 102 defines a third longitudinally extending lumen 106 for receiving therethrough the guidewire 46 (not illustrated in this instance) for implantation of the lead system after optimal pacing parameters have been determined in the manner earlier explained.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An assist device for an implantable lead system used for stimulating the body, the assist device comprising:
   a handle having a passage extending between proximal and distal ends;
   a steerable guidewire system slidably received in the passage of the handle and comprising:
   an inner conductive guidewire extending between proximal and distal ends having a peripheral outer surface and pre-shaped into a curved configuration when in the free state, the guidewire further comprising a tip electrode at the distal end thereof;
   inner insulation covering the peripheral outer surface of the conductive guidewire;
   a generally straight outer sheath coaxial with the conductive guidewire and slidable relative thereto between a first position completely receiving the conductive guidewire and thereby restraining the conductive guidewire to a straight condition and a second position withdrawn from a freed length of the conductive guidewire allowing the freed length to assume its free state curved condition;
   wherein the handle comprises a collar movable along the handle and attached to the outer sheath for manually moving the outer sheath between the first and second positions with longitudinal movement along the elongated handle; and further comprising:
   an electrical terminal in electrical continuity with the tip electrode.

2. An assist device as set forth in claim 1 wherein the lead system comprises:
   an elongated tubular lead body of flexible resilient insulative material extending between proximal and distal ends and having a longitudinally extending lumen;
   a distal tip electrode attached to the distal end of the lead body; and
   a coil conductor received in the lumen of the lead body extending between the proximal and distal ends thereof and being joined at the proximal end to an electrical connector for selective connection to a cardiac stimulation device, the coil conductor defining a second longitudinally extending lumen for receiving a guidewire therethrough for implantation of the lead system after optimal pacing parameters have been determined.

3. An assist device as set forth in claim 2:
   wherein the lead body is composed of a flexible polymeric insulating material.

4. An assist device as set forth in claim 3:
   wherein the flexible polymeric insulating material is at least one of silicone rubber, polyurethane, PTFE, and ETFE.

5. An assist device as set forth in claim 1:
   wherein the lead system comprises:
   an elongated tubular lead body of flexible resilient insulative material extending between proximal and distal ends and having a first longitudinally extending lumen;
   a distal tip electrode attached to the distal end of the lead body;
   an elongated tubular member of flexible resilient insulative material received in the first lumen of the tubular lead body and having a second longitudinally extending lumen for receiving a guidewire therethrough for implantation of the lead system after optimal pacing parameters have been determined; and
   a plurality of insulated cable conductors received in the lumen of the tubular lead body and extending between the proximal and distal ends thereof.

6. An assist device as set forth in claim 5:
   wherein the lead body is composed of a flexible polymeric insulating material.

7. An assist device as set forth in claim 6:
   wherein the flexible polymeric insulating material is at least one of silicone rubber, polyurethane, PTFE, and ETFE.

8. An assist device as set forth in claim 1:
   wherein the lead system comprises:
   an elongated tubular lead body of flexible resilient insulative material extending between proximal and distal ends and having a first longitudinally extending lumen;
   an elongated tubular member of flexible resilient insulative material having a second longitudinally extending lumen coaxial with the first longitudinally extending lumen, the tubular member having an outer diameter smaller than the inner diameter of the lead body thereby defining an annular cavity;
   an inner coil conductor within the second longitudinally extending lumen and extending between the proximal and distal ends thereof; and
   an outer coil conductor within the annular cavity and extending between the proximal and distal ends thereof;
   the inner coil conductor defining a third longitudinally extending lumen for receiving a guidewire therethrough for implantation of the lead system after optimal pacing parameters have been determined.

9. An assist device as set forth in claim 8:
   wherein the lead body is composed of a flexible polymeric insulating material.

10. An assist device as set forth in claim 9:
    wherein the flexible polymeric insulating material is at least one of silicone rubber, polyurethane, PTFE, and ETFE.

11. An assist device as set forth in claim 1:
    wherein the lead system comprises:
    an elongated tubular lead body of flexible resilient insulative material having first and second longitudinally extending lumina;
    a coil conductor within the first longitudinally extending lumen and extending between the proximal and distal ends thereof; and
    a cable conductor received in the second lumen and extending between the proximal and distal ends thereof;
    the coil conductor defining a third longitudinally extending lumen for receiving a guidewire therethrough for implantation of the lead system after optimal pacing parameters have been determined.

12. An assist device as set forth in claim 11:
    wherein the lead body is composed of a flexible polymeric insulating material.

13. An assist device as set forth in claim 12:
    wherein the flexible polymeric insulating material is at least one of silicone rubber, polyurethane, PTFE, and ETFE.

14. A method of implanting a lead system for use with an implantable stimulation device, the method comprising:
    providing a steerable guidewire comprising an inner conductive guidewire extending between proximal and distal ends and pre-shaped into a curved configuration when in the free state, and further comprising a tip electrode at the distal end of the guidewire;

advancing the guide wire through a patient's body so the tip electrode arrives at one or more locations;

performing electrical measurements to determine the efficacy of the one or more locations;

selecting a location based on the electrical measurements; and advancing a lead over the guidewire to the selected location.

15. A method of implanting a lead system as set forth in claim 14 and further comprising:

slidably removing the guidewire from the lead.

16. An assist system for an implantable lead system used for stimulating the body, the assist device comprising:

a handle having a passage extending between proximal and distal ends;

a steerable guidewire system slidably received in the passage of the handle and comprising:

an inner conductive guidewire extending between proximal and distal ends having a peripheral outer surface and pre-shaped into a curved configuration when in the free state, and further comprising a tip electrode at the distal end;

inner insulation covering the peripheral outer surface of the conductive guidewire;

a generally straight outer sheath coaxial with the conductive guidewire and longitudinally slidable relative thereto between a first position completely receiving the conductive guidewire and thereby restraining the conductive guidewire to a straight condition and a second position withdrawn from a freed length of the conductive guidewire allowing the freed length to assume its free state curved condition;

a collar on the elongated handle that is movable along the handle and attached to the outer sheath for manually moving the outer sheath between the first and second positions with longitudinal movement along the elongated handle;

an electrical terminal in electrical continuity with the tip electrode;

a reference electrode adapted for placement in the body at a location spaced from the tip electrode; and a pacing system analyzer connected between the electrical terminal and the reference electrode in the body and operable to seek a location at which optimal pacing parameters can be determined prior to final implantation of the lead system.

* * * * *